Figure 1:
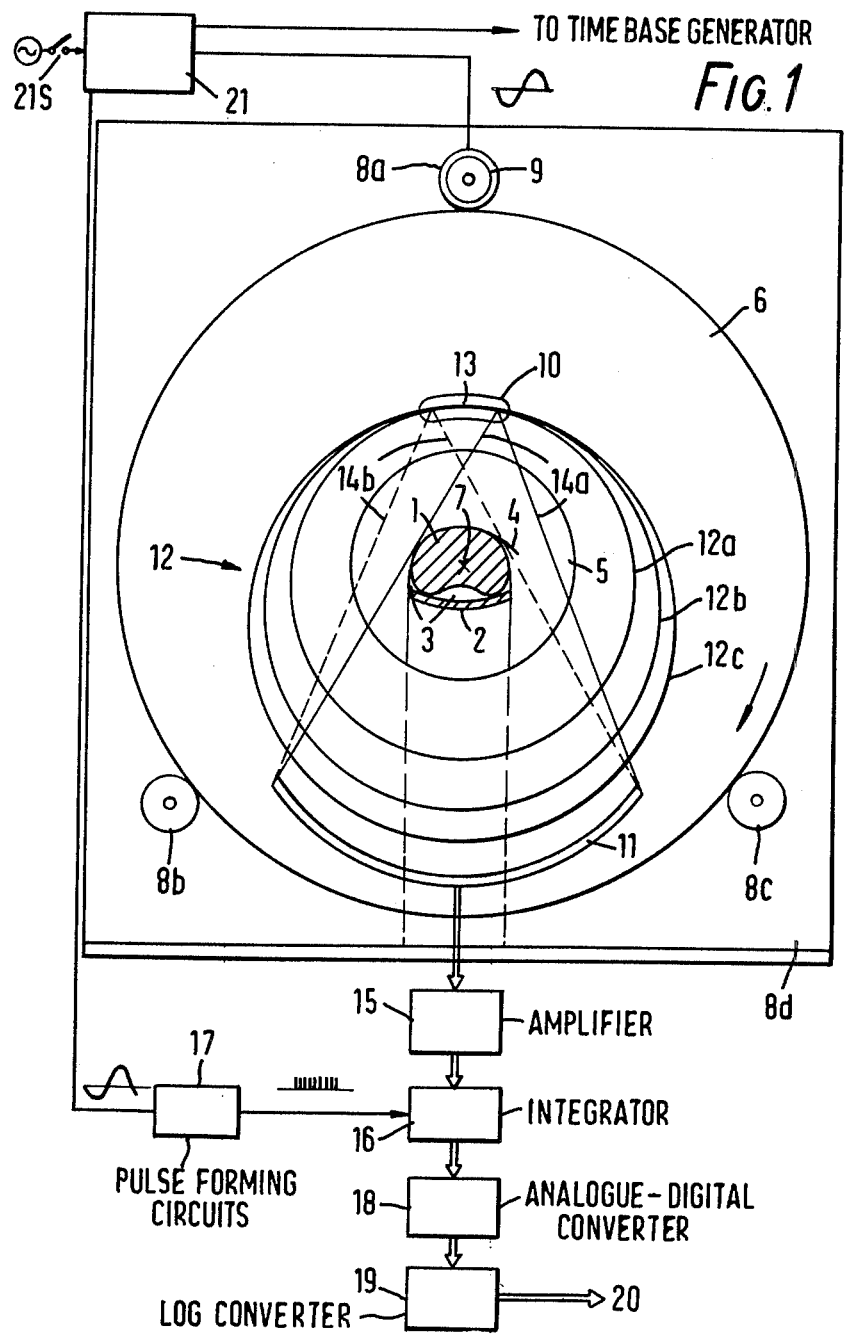

United States Patent [19]

LeMay

[11] 4,091,289

[45] May 23, 1978

[54] RADIOGRAPHY

[75] Inventor: Christopher Archibald Gordon LeMay, Osterley, England

[73] Assignee: EMI Limited, Hayes, England

[21] Appl. No.: 762,521

[22] Filed: Jan. 26, 1977

[30] Foreign Application Priority Data

Feb. 3, 1976 United Kingdom ................ 4134/76

[51] Int. Cl.² .............................................. G03B 41/16
[52] U.S. Cl. .................................. 250/445 T; 250/511
[58] Field of Search .................. 250/445 T, 505, 511, 250/512, 513, 514, 508, 509

[56] References Cited

U.S. PATENT DOCUMENTS

| | | |
|---|---|---|
| 3,944,833 | 3/1976 | Hounsfield ........................ 250/445 T |
| 4,041,315 | 8/1977 | Hounsfield ........................ 250/445 T |

Primary Examiner—Craig E. Church
Attorney, Agent, or Firm—Cooper, Dunham, Clark, Griffin & Moran

[57] ABSTRACT

In a computerized tomographic apparatus in which relative movement occurs between a fan of radiation and a bank of detectors, at least some of the detectors are required to receive radiation over a range of angles of incidence while at the same time being insensitive to scattered radiation. A dynamic collimating arrangement is described which enables each detector to accommodate said relative movement but nevertheless intercepts a substantial amount of scattered radiation.

10 Claims, 2 Drawing Figures

RADIOGRAPHY

The present invention relates to radiography, and it relates especially, though not exclusively, to that branch of radiography which is known as computerised axial tomography (or briefly C.A.T.), in whcih the object is to produce a representation of the absorption coefficients, with respect to penetrating radiation (such as X-radiation), at a plurality of elemental areas distributed over a slice cross-sectionally disposed in a body.

One example of an apparatus for performing C.A.T. is disclosed and claimed in U.S. Pat. No. 3,778,614. In general such apparatus comprises a source of radiation, detector means responsive to the radiation and an arrangement for scanning the source, and usually also the detector means, relative to a body so that radiation emergent from the body along many substantially coplanar paths is detected by said detector means to provide respective absorption values indicative of the overall absorption suffered by the radiation on traversing each of said paths through the body. The absorption values so provided are processed, for example in the manner described in U.S. Pat. No. 3,778,614 or in the manner disclosed in U.S. Pat. No. 3,924,129, to evaluate the aforementioned coefficients.

As such apparatus has developed, a requirement for rapid acquisition of the absorption values has become evident and this, of course, implies a more rapid scanning operation. In one example described in the aforementioned patent specification, the scanning is effected by means of a combination of lateral and rotational scanning movements. One way of effecting more rapid acquisition of the absorption values is to cause the source to produce a fan-like, planar swath of radiation of sufficient breadth to substantially encompass the body in the plane of investigation. The lateral scanning movement can then be dispensed with and the rotational movement only retained. However difficulties arise in implementing such an apparatus in practice because it is necessary to use a large number of detectors extended across the breadth of the swath of radiation on the opposite side of the body to the source, and these detectors tend to exhibit different initial sensitivities and different sensitivity variations as the scanning proceeds. The detectors commonly used for this purpose comprise scintillator crystals optically coupled either to photomultipliers or to photo-diodes. The aforementioned sensitivity and sensitivity variation differences as between detectors can cause errors in the evaluation of the aforementioned coefficients.

It is desirable that the aforementioned errors be reduced or eliminated whilst retaining a capability for rapid data acquisition, and in U.S. application No. 630,779 and 733,941 there are disclosed respective techniques for effecting such reduction or elimination, both techniques involving a re-introduction of a lateral scanning movement, but one which is effected by electronically scanning the electron beam of an X-ray generating tube across a suitably shaped anode, and is thus effected so rapidly that the rotational scanning movement can proceed uninterrupted. The lateral scanning movement is synchronised with the rotational scanning movement as described in either of said U.S. application Nos. 630,779 and 733,941.

A difficulty can arise with these arrangements, however, and with other arrangements in which there is relative movement between a fan of radiation and a bank of detectors, due to the reception by said detector means of scattered radiation, as opposed to radiation transmitted directly through the body along the paths in question. It has been the practice to provide collimators for the detectors so that such scattered radiation cannot, in general, reach them. However, when relative movement occurs between a fan of radiation on one hand and detectors on the other hand the detectors, or at least a substantial number of them, have to be capable of receiving radiation from the source point when the latter is at several different positions in relation thereto. This means that the collimators for those detectors, if fixed, have to be wide enough to accommodate the entry of radiation from all of said several source point positions. Conversely, of course, this increases the susceptibility of those detectors to the receipt of scattered radiation and it also exacerbates the already difficult physical problem of disposing the required large number of detectors and collimators in such a way that no component of one detector/collimator assembly impedes the ingress of radiation into another assembly.

It is an object of this invention to overcome, or at least reduce, the difficulty described in the last preceding paragraph.

According to the invention there is provided radiographic apparatus including a source of a substantially planar spread of penetrating radiation, such as X-radiation, detector means responsive to said radiation for detecting the radiation after it has passed through a body under examination, scanning means for scanning at least said source around the body about an axis intersecting said spread of radiation, means for causing relative movement to occur between said spread of radiation and said detector means and collimator means including a plurality of apertured members, each including a respective part disposed between said body and the detector means, said parts being disposed so that they are successively encountered by said radiation, and means for moving said members at respective, different rates across said spread of radiation, said rates being influenced by the rate at which said scanning is executed, the rate of said relative movement and the proximity of the respective part to said detector means, whereby said apertured members as a whole act as a dynamic collimator arrangement for said detectors.

Figure 2:
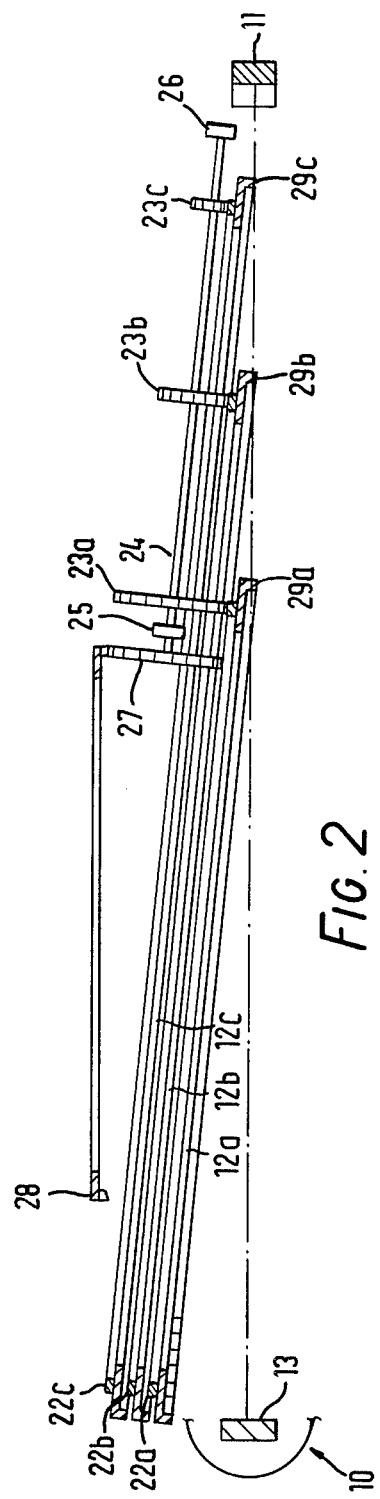

In order that the invention may be clearly understood and readily carried into effect, one embodiment thereof will now be described, by way of example only, with reference to the accompanying drawings of which:

FIG. 1 shows, in front elevation, an apparatus incorporating one example of the invention, and FIG. 2 shows, in more detail but not to scale, part of the apparatus shown in FIG. 1.

Referring to FIG. 1 there is shown therein an apparatus incorporating one example of the invention. A body 1 to be examined, shown in transverse section, is supported on a suitably shaped bed 2, also shown in tranverse section. A material 3, having an absorption to the radiation similar to that of body tissue, is positioned between the body 1 and the bed 2, to substantially exclude air from the gap therebetween, and is extended partly about the body to provide an approximately circular cross-section to the radiation. The body is retained firmly in the desired position by means such as a retaining strap 4. If desired a more rigid retaining means, such as the two part ring described in U.S. Pat. No. 3,937,963 may be used.

The bed 2 and the body 1 are inserted into an aperture 5 in a rotatable member 6 so that a desired part of the body is centred in the aperture. The rotatable member 6 is arranged to rotate around the body 1 about an axis 7, longitudinal of the body 1 and perpendicular to the paper, central to the aperture 5. For that purpose it is supported by three gear wheels 8 a,b,c, which engage with gear teeth, not shown, cut into the periphery of member 6. The gear wheels 8 are journalled in a main frame 8d of the apparatus, which frame may take any form suitable to support the apparatus and to allow the necessary rotation. Gear wheel 8a is driven by a synchronous electric motor 9, also mounted on the main frame, the operation of which will be described hereinafter.

The rotatable member 6 also carries a source of X-rays 10 and a bank of detectors 11. Associated with the detectors are a plurality of apertured rings, generally shown at 12, which are moved, in a manner which will be described more fully hereinafter, at different speeds across the spread of radiation to provide, in effect, a dynamic collimator for said detectors. Three rings 12a, 12b and 12c, are used in this example of the invention, and it will be observed that each ring includes a respective part disposed between the body 1 and the detector 11, and that the radiation emergent from the body 1 encounters successive ones of the ring parts on its way to the detectors 11. Clearly only when apertures in all three rings are aligned with a given beam path through the body 1 will the radiation be able to reach the relevant detector for that path. The detectors, which in a typical embodiment number 120, can be of any suitable type, for example scintillation crystals with associated photomultipliers or photodiodes.

The source 10 includes an elongated target/anode 13, which ideally is shaped to conform to part of the circle passing through the arc of detectors 11, and which will be discussed further hereinafter, and provides a planar, fan-shaped spread 14 of X-rays from a substantially point origin which can be scanned by electronic means from the position 14a to the position 14b shown. In this example the corresponding scan of the substantially point origin of the X-rays along target 13 is of the order of 10cm. The detectors are nominally arranged so that they receive radiation which has traversed beam paths which are angularly spaced by about $\frac{1}{3}°$ from each other.

In this example the X-ray source 10 is placed of the order of 52cm from the central axis 7 with the detectors 11 being placed a further 70cm. on the opposite side of axis 7 so as to intercept the radiation of fan 14 for any position of the point of origin of the X-rays in its lateral scan along target 13. As mentioned above the detectors and source preferably lie along arcs of a single circle which in this example, however, is not concentric with axis 7. It should be understood that the purpose of the collimator arrangement 12 is to prevent, so far as is possible, the reception by the detectors 11 of scattered radiation. Although, in this example, the distance between source 10 and axis 7 is three-quarters of that between detectors 11 and axis 7, the relationship is for the purpose of satisfying a particular design criterion, and if desired the source and detectors may be placed equidistant from the axis or in any other desired relationship.

Disregarding for the moment the rotary motion referred to hereinbefore, the arrangement is such that the point of origin of the X-rays is scanned steadily along target 13, taking the fan of X-rays from 14a to 14b, and is rapidly returned to the starting point before repeating the scan. During the time of one such scanning movement, each detector of array 11 provides an output signal indicative of the intensity of radiation incident thereon. Each detector feeds a respective pre-processing circuit including an amplifier 15 and an integrator 16, in which the output signals are integrated over periods determined by a series of pulses from pulse forming circuits 17. In this example the timing of the pulse is such that there are forty-eight integration periods in the time of one lateral scan of X-ray fan 14 from 14a to 14b. Thus each detector measures radiation in effect along forty-eight narrow beams joining that detector with forty-eight equally spaced positions along target 13.

Hereinafter the word "beam" will be used to denote a beam of radiation incident on a detector and scanned with the source and detectors. Conversely the path through the body irradiated by a beam, and fixed in relation to the body, will be termed a "beam path". The paths are, of course, of width determined by the integration intervals and are of a shape determined by the geometry of scanning movements in those intervals. For the purposes of illustration, however, they may be considered to be represented by single lines which represent their centre lines. The lines illustrating the extremes of fan 14 are in fact the centre lines of the extreme beams of the fan.

Signals representing the intensity of radiation received along such paths are converted to digital form in converters 18 and to logarithmic form in converters 19, which components are also included in the pre-processing circuits, for output at 20 for further processing. It will be understood that one amplifier 15, integrator 16, A/D converter 18 and log converter 19 is provided for every detector, all operated in synchronism. The processing may, if desired, sort the signals into sets representing absorption along sets of parallel paths for processing by a suitable method such as that described in U.S. Pat. No. 3,924,129 to provide the desired representation. The circuits 15 to 19 are of well known construction.

The motor 9 causes rotatable member 6 to execute a continuous motion, in the direction shown by the arrow, about axis 7 and therefore about the body 1 of the patient on bed 2. The rotary motion and the lateral scanning of X-ray fan 14 must be in a strict relationship to achieve the desired result. Synchronous motor 9 is driven by a periodic sinusoidal voltage from a power supply 21 and, after suitable period of time, stabilises in synchronisation with that sinusoidal voltage. It will be appreciated that, when under load, the motion of motor 9 lags the phase of the sinusoidal voltage but this is not significant provided the load does not change and therefore the lag is constant. The sinusoidal voltage from supply 21 is supplied to a time base generator (not shown) where it provides a periodic sawtooth waveform voltage, to operate the scanning of source 10, and also to unit 17 which converts it to square pulses of the same phase and generates therefrom the series of pulses, in strict phase relationship with the sinusoidal voltage, to clear and read integrators 16 as explained hereinbefore. Pulse forming circuit 17 operates in a conventional manner by any suitable means known in the art. Flyback of the sawtooth waveform takes place during selected resetting periods of the integrators.

More detail as to the inter-relationship of the lateral and rotational scanning movements and the processing and other considerations can be found in the aforementioned U.S. application No. 630,799 to which the reader's attention is invited. However it is considered that further discussion of such detail in this application would not assist the reader in understanding the present invention, so no further references thereto will be made herein.

Referring now to FIG. 2, there is shown in more detail, but not to scale, the collimator arrangement 12 of FIG. 1. In addition a few other components, bearing the same reference numerals as they bore in FIG. 1, have been included to assist the correlation of FIGS. 1 and 2.

As will be seen, the three rings 12a, 12b and 12c are inclined at a common angle to the plane of the spread of radiation produced by the source 10. They are disposed one above the other, and their rotational axes are parallel, but not coincident. In theory, for proper operation, the rings should all pass through the anode 13 of the tube 10, but of course in practice this is not possible and the slight inclination of the rings necessary to avoid fouling the tube is not of significance. Each collimator ring is formed with an annular gear wheel 22a, 22b, 22c respectively, and it is by means of these wheels that the rings are rotated. Each wheel 22 co-operates with a respective driving gear wheel 23, the wheels 23 being mounted on a common drive shaft 24 which can rotate in bearings 25 and 26 fixed to the rotatable member 6 (FIG. 1). The shaft 24 is driven by way of a further gear wheel 27 which is mounted thereon but does not contact any of the wheels 22. Instead the wheel 27 is driven by a main drive wheel 28 which is fixed and is disposed parallel to the member 6. The wheel 27 is identical to the wheel 23a and the ratios of gear teeth and wheel diameters are chosen to suit the parameters of the apparatus in hand. In the present example, the relevant features are given in the following table:

| Component | Diameter(cm) | Number of teeth |
|---|---|---|
| Wheel 22a | 90.00 | 1500 |
| Wheel 22b | 102.60 | 1710 |
| Wheel 22c | 110.40 | 1840 |
| Wheel 23a | 12.00 | 200 |
| Wheel 23b | 6.84 | 114 |
| Wheel 23c | 5.52 | 92 |
| Wheel 27 | 12.00 | 200 |
| Wheel 28 | 60.00 | 1000 |

All of the rings 12 bear skirts 29a, 29b, 29c respectively which depend into the paths of radiation from the source to the detectors, and each skirt is formed with 540 collimator apertures, these being disposed at diameters 92.100, 105.257 and 113.353 cm. respectively, i.e. somewhat larger in each case than the respective wheel 23. It will be appreciated that, since the ring 12a is nearest the source 10, the ring 12a rotates faster than the ring 12b which, in turn, rotates faster than the ring 12c.

It will be appreciated from the foregoing that the source of radiation, as seen from a given detector, moves smoothly through a small angle (corresponding to the aforementioned movement of about 10cm) and then jumps back to its starting point. The above described arrangement moves the rings 12 at suitable speeds to allow beams from the source to reach each detector during the steady motion, and the number of collimator rings and their dimensions are selected so that, when the source flies back to its starting point, it is re-aligned with each detector via a respective, different combination of apertures.

Thus, the arrangement is such that a beam from the source to a given detector traverses a respective aperture in each of the rings 12, and, during the period when the smooth scanning movement of the source is effected, the relative movement of the three rings accommodates the movement of the source; the beam passing through the same three apertures for all positions during a single one of the smooth scanning movements.

The physical dimensions and the relative rates of movement of the rings, as well as the number of apertures required in each ring for different sets of circumstances can be calculated from the relevant geometry, and it is stressed that the scope of this invention is not limited to the example which has been described.

The rings 12 are supported on respective bearings (not shown) which are mounted on the rotatable member 6 and, if such bearings are not transmissive of the x-radiation, they are preferably disposed outside the bounds occupied by the fan of radiation.

Modifications may be made to the apparatus shown in the drawings without departing from the scope of the invention. For example suitable attenuators may be placed between the source 10 and the body 1 and/or between the body 1 and the detectors 11 to allow for the different thicknesses of body material traversed by beams near the edges of the spread of radiation produced by source 10 as compared with that traversed by beams at or near the centre of the spread. Furthermore, if desired, a photo-electric cell may be mounted adjacent one end of the array 11 of the detectors, and in the same plane, but outside the extremities of the spread of radiation. A light source is mounted between the body 1 and the inner ring 12a so that it projects a beam of light towards the photocell. This beam of light is arranged to be substantially parallel to the extreme right-hand beam of the spread of radiation when the latter assumes the position 14a, and the beam of light therefore comprises a "dummy" beam which can be used to trigger the flyback movement of the electron beam of tube 10. This is possible because the changing aspect of the collimator produced by the three rings permits light to fall on the photo-cell just after the extreme right hand beam of radiation has assumed the position 14a. Prior to said beam of radiation assuming said position, one or more of the rings 12 is always disposed to interrupt the beam. Thus, the flyback is initiated at the moment the beam of light impinges on the photo-cell. The arrangement ensures accurate registration between the movements of the rings 12 and the scanning of the spread of radiation.

As mentioned previously, the sensitivity of the detectors used tends to drift. It is therefore preferable that the said sensitivity is checked frequently by comparison with a datum value. One way in which this can be achieved is as follows.

The active scan, i.e. the angular movement effected during the exposure of the patient to the X-radiation, extends over (in this example) 220°. The apparatus is arranged to start in a position such that the source 10 is behind a screen (not shown) which substantially prevents the irradiation of the body 1. At this time, the detectors should be producing a zero reading and all the detector readings can be noted. After the 220° scanning movement has been effected, the source 10 is again arranged to pass behind the screen so that the zero readings can again be checked.

Arrangements involving the use of a standard attenuator (not shown) in the path of radiation outside the normal spread indicated by the bounds 14 to one or more special detectors can be used to compensate for changes in the gain of the detectors in the array 11.

If there is difficulty in maintaining the required accuracy of the amplitude of the waveform used to scan the electron beam of the tube 10 over the anode 13 thereof, (and hence of the position of the spot opposite the moving collimators) it is possible to generate a "servo control" voltage which may be added to the scan waveform so as to provide a continuous correction.

This servo control voltage can be generated by superimposing, on the scan waveform, a relatively high frequency voltage so that the spot wobbles with a small amplitude, say $1/2000^{th}$ of the scan amplitdue, at a frequency (say) 1,000 times the scan frequency. A connection is made to each X-ray detector via a filter which is able to separate out this frequency. The separated outputs from all of the detectors are then combined, amplified and passed to a phase sensitive detector which is also fed with a reference voltage derived from the spot wobble voltage.

If the spot is lined up with the collimator system, then there will be no output from the detectors at the wobble frequency. However if, when the spot moves, parts of the collimator system cast shadows on the detectors, then the detectors will indicate this by giving an output. This output will indicate the direction of the error, and can thus be combined with the scan waveform to effect a servo action. Thus, the output of the phase sensitive detector, suitably amplified, can provide a correction in the form of a voltage to re-align the spot with the collimator system.

What I claim is:

1. Radiographic apparatus including a source of a substantially planar spread of penetrating radiation, such as X-radiation, detector means responsive to said radiation for detecting the radiation after it has passed through a body under examination, scanning means for scanning at least said source around the body about an axis intersecting said spread of radiation, means for causing relative movement to occur between said spread of radiation and said detector means, and collimator means including a plurality of apertured members, each including a respective part disposed between said body and the detector means, said parts being disposed so that they are successively encountered by said radiation, and means for moving said members at respective, different rates across said spread of radiation, said rates being influenced by the rate at which said scanning is executed, the rate of said relative movement and the proximity of the respective part to said detector means, whereby said apertured members as a whole act as a dynamic collimator arrangement for said detectors.

2. Apparatus according to claim 1 wherein said scanning means also scans said detector means around the body about said axis.

3. Apparatus according to claim 2 wherein said means for causing relative movement includes means causing said spread of radiation to execute lateral scanning movements relative to the body, said lateral scanning movements being synchronised to said scanning.

4. Apparatus according to claim 1 wherein said apertured members comprise skirts dependent from respective rings, said rings being of differing diameters.

5. Apparatus according to claim 4 wherein said rings are three in number.

6. Apparatus according to claim 4 wherein each ring is formed with a respective annular gear wheel and wherein a drive system for said rings includes a shaft bearing a respective driving gear wheel arranged to mesh with each of said annular gear wheels.

7. Apparatus according to claim 6 wherein said shaft is driven by a further drive wheel which meshes with a stationary, annular gear, said further wheel being moved relative to said stationary gear by said scanning means.

8. A medical radiological apparatus for examining a patient comprising:
a source disposed on one side of the patient and irradiating the patient with X-radiation fanning out substantially in a plane when moving downstream from the source;
detectors of said radiation disposed in a row in said plane on the other side of the patient to receive and detect radiation from the source which has passed through the patient;
means for orbiting at least the source around the patient and for moving the source relative to the detectors; and
a dynamic collimator system comprising:
a plurality of members each having a portion disposed downstream of the patient in the path of the radiation received by the detectors, each of said portions having X-ray transparent and X-ray opaque areas alternating in the direction in which the row of detectors extends; and
means for moving at least said portions of the members, at respective different rates, relative to the radiation to align only X-ray transparent areas of the members along each of a numer of lines connecting the source with a corresponding number of detectors at selected relative positions of the source and detectors.

9. An apparatus as in claim 8 where each of said members comprises a ring having a flange, a part of each flange being disposed in the path of the radiation received by the detectors and forming said member portion, each flange having a row of said X-ray opaque and X-ray transparent areas, and where the moving means comprise means for rotating each of said rings about an axis different from that of any other ring.

10. An apparatus as in claim 8 where the moving means comprise means for moving the member portions to align an X-ray transparent area of each of the member portions concurrently along a number of said lines.

* * * * *